US011827861B2

(12) United States Patent
Diemund et al.

(10) Patent No.: US 11,827,861 B2
(45) Date of Patent: Nov. 28, 2023

(54) FLOATING PHOTOBIOREACTORS FOR ALGAE BIOFUEL PRODUCTION AND DEVICES AND METHODS RELATED THERETO

(71) Applicant: ExxonMobil Technology and Engineering Company, Annandale, NJ (US)

(72) Inventors: Mark A. Diemund, Houston, TX (US); Patrick L. Hanks, Bridgewater, NJ (US); Sarah E. Feicht, Raritan, NJ (US)

(73) Assignee: EXXONMOBIL TECHNOLOGY AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 17/816,463

(22) Filed: Aug. 1, 2022

(65) Prior Publication Data

US 2023/0045239 A1 Feb. 9, 2023

Related U.S. Application Data

(60) Provisional application No. 63/203,904, filed on Aug. 4, 2021.

(51) Int. Cl.
*C10L 8/00* (2006.01)

(52) U.S. Cl.
CPC .......... *C10L 8/00* (2013.01); *C10L 2200/0469* (2013.01); *C10L 2290/36* (2013.01); *C10L 2290/56* (2013.01)

(58) Field of Classification Search
CPC ......... C10L 2200/0469; C10L 2290/36; C10L 2290/56; C10L 8/00; C25B 1/00; C25B 1/04; C25B 1/23; C25B 11/031; C25B 11/032; C25B 11/036; C25B 15/02; C25B 15/08; C25B 9/17; C25B 9/75; Y02E 60/36
See application file for complete search history.

(56) References Cited

U.S. PATENT DOCUMENTS

| | | | |
|---|---|---|---|
| 8,409,845 B2 | 4/2013 | Trent et al. | |
| 2011/0159581 A1* | 6/2011 | Zhang | C12M 23/34 435/292.1 |
| 2013/0337518 A1* | 12/2013 | Razavi-Shirazi | C02F 3/34 435/141 |

FOREIGN PATENT DOCUMENTS

WO WO-2015133364 A1 * 9/2015 ............. B01D 69/02

OTHER PUBLICATIONS

WO2015133364A1 English Translation (Year: 2015).*
(Continued)

*Primary Examiner* — Ellen M McAvoy
*Assistant Examiner* — Chantel Graham
(74) *Attorney, Agent, or Firm* — SHOOK, HARDY & BACON L.L.P.

(57) ABSTRACT

Apparatuses including offshore porous floating bioreactors for containing algae water slurries in a saltwater environment. The porous floating bioreactors include a top portion and a bottom portion. At least a portion of the top portion is composed of a first transparent material and at least a portion of the bottom portion is porous. The offshore porous floating bioreactors may be deployed in a saltwater environment to facilitate one or both of cultivation or lipid induction of an algae water slurry contained therein.

20 Claims, 5 Drawing Sheets

(56) References Cited

OTHER PUBLICATIONS

"Algae Photobioreactor Using Floating Enclosures With Semi-Permieable Membranes", Natioal Aeronautics and Space Administration, www.nasa.gov.

* cited by examiner

FLOATING PHOTOBIOREACTORS FOR ALGAE BIOFUEL PRODUCTION AND DEVICES AND METHODS RELATED THERETO

CROSS-REFERENCE TO RELATED APPLICATIONS

This application claims the benefit of U.S. Provisional Application No. 63/203,904, filed on Aug. 4, 2021, the entire contents of which are incorporated herein by reference.

FIELD OF THE INVENTION

The present disclosure relates to algae biofuel production and devices and methods related thereto and, more particularly, to floating photobioreactors for utilizing a saltwater carbon source.

BACKGROUND OF THE INVENTION

Concerns about climate change, carbon dioxide ($CO_2$) emissions, and depleting mineral oil and gas resources have led to widespread interest in the production of biofuels from algae, including microalgae. As compared to other plant-based feedstocks, algae have higher $CO_2$ fixation efficiencies and growth rates, and growing algae can efficiently utilize wastewater, biomass residue, and industrial gases as nutrient sources.

Algae are photoautotrophic organisms that can survive, grow, and reproduce with energy derived from the sun through the process of photosynthesis. Photosynthesis is a carbon recycling process through which inorganic $CO_2$ combines with solar energy, other nutrients, and cellular biochemical processes to output gaseous oxygen and to synthesize carbohydrates and other compounds critical to the life of the algae.

To produce algae biomass in outdoor environments, algae is generally grown in a water slurry using one or more open pond systems, which are typically oval in shape (e.g., pill-shaped) and referred to as "raceway ponds." The water slurry comprises selected nutrients and the pond system circulates the algae in the water slurry to ensure adequate exposure to solar energy, thereby promoting the growth of algae biomass. Various downstream processing methods are used to separate the algae biomass and extract lipids therefrom for the production of biofuel and other oil-based and non-oil-based products, including nutraceuticals, pharmaceuticals, cosmetics, chemicals (e.g., paints, dyes, and colorants), fertilizer and animal feed, and the like. The remaining wastewater and biomass residue can be recycled or otherwise used in a variety of sustainable applications. For example, the wastewater can form some or all of a subsequent water slurry and the biomass residue can be used as animal feed.

Because the processing of algae biomass produces valuable commodities, including sustainable biofuels, large-scale cultivation of algae is desirable. However, to compete merely with U.S. diesel demand, a single algae biofuel facility would likely need to produce at least 10 thousand barrels per day (kbd), or even more (e.g., 20 kbd), to be viable, which is on par with current refinery facilities producing petroleum products. Accordingly, the total area of an outdoor environment system for true commercial algae biomass cultivation would need to be extremely large, requiring large vessels covering hundreds, or even thousands, of total surface area land acreage—thus, competing with available land space for human use and food production, and requiring expensive large scale facility footprints.

SUMMARY OF THE INVENTION

The present disclosure relates to algae biofuel production and devices and methods related thereto and, more particularly, to floating photobioreactors for utilizing a saltwater carbon source.

In some aspects, an apparatus is provided including an offshore porous floating bioreactor for containing an algae water slurry in a saltwater environment and having a top portion and a bottom portion. At least a portion of the top portion is composed of a first transparent material and at least a portion of the bottom portion is porous, comprising a plurality of pores.

In some aspects, a method is provided including deploying at least one offshore porous floating bioreactor in a saltwater environment and performing at least one of cultivation or lipid induction of an algae water slurry contained in the at least one offshore porous floating bioreactor. The offshore porous floating bioreactor includes a top portion and a bottom portion. At least a portion of the top portion is composed of a first transparent material and at least a portion of the bottom portion is porous, comprising a plurality of pores.

BRIEF DESCRIPTION OF THE DRAWINGS

The following figures are included to illustrate certain aspects of the disclosure, and should not be viewed as exclusive configurations. The subject matter disclosed is capable of considerable modifications, alterations, combinations, and equivalents in form and function, as will occur to those skilled in the art and having the benefit of this disclosure.

DETAILED DESCRIPTION OF THE INVENTION

The present disclosure relates to algae biofuel production and devices and methods related thereto and, more particularly, to floating photobioreactors for utilizing a saltwater carbon source.

Biofuel production from cultivated algae slurries offers sustainable energy solutions to reduce reliance on fossil fuels and reduce greenhouse gas emissions. Other oil-based and non-oil-based products can additionally be derived from algae biomass. To accomplish substantial economic, environmental, and societal impact, algae must be cultivated in large-scale, industrial-sized systems. However, typical outdoor scale-up requirements necessitate large-scale ponds of great surface area, such as an area size on a magnitude of about 1 acre to about 30 acres, which may further depend on various factors such as land topography. Successful scale-up is vital to the commercial viability of an algae cultivation facility, in terms of at least operational cost control (e.g., earthworks, site preparation, pumping, mixing, water resources, land resources, nutrient resources, and the like), algae product quantity, and commercially desirable production rates. Moreover, nutrients within a cultivating algae slurry are consumed by the cultivating algae and thus require replenishment, often limiting or hindering algae growth and resulting in a significant bottleneck to large-scale, industrial sized processing. Capturing, transporting, storing, and disposing of such nutrients (e.g., carbon sources) can be particularly costly in terms of equipment requirements, energy consumption, and, again, land space requirements.

Algae growth for biofuel production, for example, requires a significant carbon supply. Typically, carbon is supplied in one of three forms: dissolved carbon dioxide, bicarbonate, and carbonate. Due to the large demand for such carbon sources, algae growth facilities must supply carbon to cultivating algae cells, which, as discussed hereinabove, may be particularly costly to the facility. Offshore saltwater sources are a generally untapped source of carbon. Because of its salinity and pH (i.e., about 8-8.2), saltwater sources generally comprise carbon in the form of bicarbonate and/or dissolved carbon which has been found to be sufficient to support algae growth and lipid production.

As used herein, the term "saltwater," with reference to offshore saltwater sources, and grammatical variants thereof, refers to ocean water and other salt water reservoirs. Typically, the saltwater described herein has a salinity in the range of about 30 parts per thousand (ppt) to about 45 ppt, encompassing any value and subset therebetween, and a pH in the range of about 7.5 to about 8.5, encompassing any value and subset therebetween.

The present disclosure provides devices and methods for utilizing one or more porous floating bioreactors that can be deployed in an offshore saltwater environment that avoids land costs and land competition associated with traditional outdoor, land-based algae cultivation systems. The porous floating bioreactors of the present disclosure are designed to utilize naturally existing carbon from the saltwater environment, thereby reducing costs associated with capturing and transporting carbon to an outdoor land-based system and other scale-up challenges. The porous floating bioreactors of the present disclosure are further designed to capitalize on the saltwater environment as a thermal reservoir, thus regulating the temperature of the bioreactors, and may be tailored to achieve desired growth rates and lipid formation rates (e.g, 10 g/m$^2$/day). Accordingly, the growth of cultivating algae is directly limited by the availability of a carbon source being replenished within the porous floating bioreactors described herein.

As used herein, the term "porous floating bioreactor," and grammatical variants thereof, refers to a porous, semi-permeable containment (enclosed) vessel having pores sized to permit fluid transfer of water, nutrients, and carbon sources thereacross, while containing algae cells therewithin. Waste products and dissolved oxygen may additionally be transported out of the porous floating bioreactor through the same pores. Therefore, the porous floating bioreactors of the present disclosure support fluid flow that promote continuous positive algae growth rates, leading to robust lipid-rich algae biomass, as described in greater detail hereinbelow.

As used herein, the term "fluid flow" or "fluid transfer," and grammatical variants thereof, refers to the movement of fluids, including liquids, gases, and solids, via a pressure, osmosis, or temperature gradient (e.g., encompassing bulk fluid flow, mass diffusion, and the like, and any combination thereof). For example, the pressure differential of naturally occurring wave action within an offshore saltwater source (e.g., seawater) may be used to drive fluid flow via a pressure differential; the salinity differential between the interior of the porous floating bioreactor and the surrounding saltwater may be used to drive fluid flow via osmosis; and the temperature differential between the interior of the porous floating bioreactor and the surrounding saltwater may be used to drive fluid flow via convection. Each of these fluid flow "drivers" may be used alone or in combination without limitation.

Figure 1:
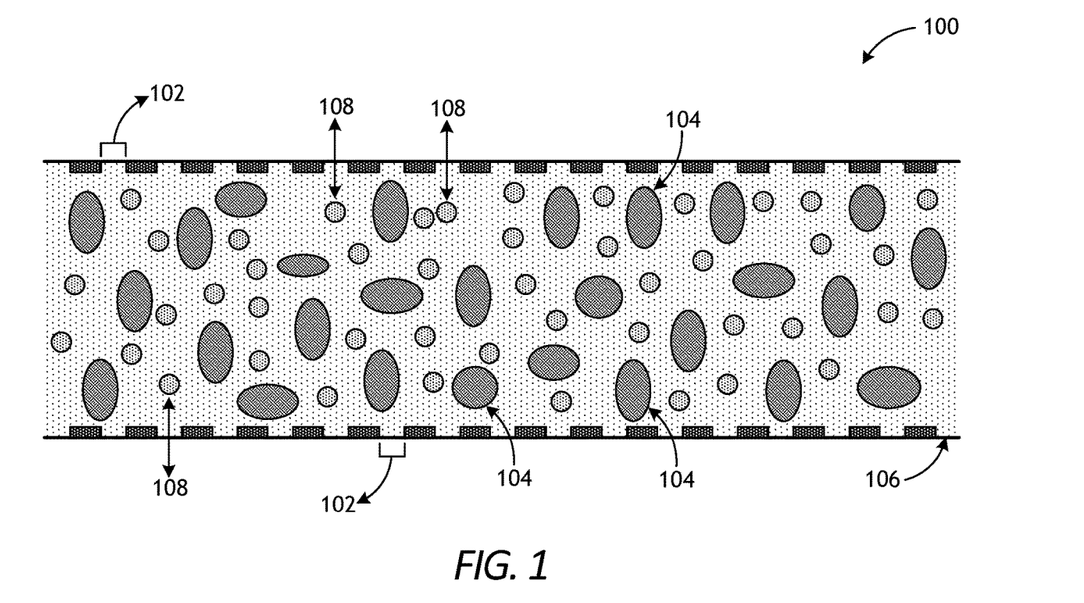
FIG. 1 is a diagram of an illustrative porous floating bioreactor according to one or more aspects of the present disclosure.

Referring to FIG. 1, provided is a diagram of an illustrative porous floating bioreactor according to various aspects of the present disclosure. As shown, porous floating bioreactor 100 comprises pores 102, which may be of the same or different sizes (e.g., in area or width, regardless of shape), through porous material 106. Water 108 and nutrients 108 are distributed throughout the interior and exterior of the porous floating bioreactor 100 and are capable of bulk transfer through the pores 102, while algae cells 104 remain in the interior of the porous floating bioreactor 100. That is, during algae growth, as well as during lipid formation, the algae cells 104 are contained within the porous floating bioreactor 100, while bulk water 108 and nutrients 108 flow into and out of the pores 102 of the porous floating bioreactor 100 from the surrounding offshore, saltwater environment in which it is floating, thereby supporting sustained algae growth, as well as lipid formation. Accordingly, the porous floating bioreactor 100 of the present disclosure is able to continually increase algae biomass with no additionally supplied nutrients or carbon sources, which are supplied via bulk transfer through the pores 102 from the surrounding offshore, saltwater environment. Moreover, the algae cells are contained within the porous floating bioreactor 100 at all times, thus facilitating algae separation and harvesting activities upon the algae 104 reaching the desired confluency and/or lipid concentration.

The porous floating bioreactors of the present disclosure may be composed of a suitable porous, semi-permeable material capable of deployment in an offshore environment (e.g., resistant or otherwise capable of use in environments having high salinity, turbidity, marine life), which will depend on the particular offshore saltwater location in which the porous floating bioreactor it is to be deployed. Examples of suitable materials include, but are not limited to, polyethylene (including ultra-high molecular weight polyethylene, high-density polyethylene, low-density polyethylene, very-low-density polyethylene, and the like), cellulose acetate, polypropylene, polyvinyl chloride, ethylene vinyl acetate, polyurethane, nylon, polyvinyl acetate, polytetrafluoroethylene, and the like, and any combination thereof. In some instances, the selected material may be woven or non-woven, depending on the particular pore size desired for the porous floating bioreactor and/or depending on whether the material is intended to be porous or not (e.g., the top portion of the bioreactor may not be porous in some instances). In one or more aspects of the present disclosure, the porous floating bioreactor is composed of non-woven polyethylene, cellulose acetate, and any combination thereof.

The selected material for the porous floating bioreactor is transparent at least at a top portion that is exposed to sunlight. This top portion may include the top half of the porous floating bioreactor, for example, or a portion that is less than half and is exposed to sunlight. The transparent top portion of the porous floating bioreactor may remain slightly above the surface of a saltwater environment in which it is floating, rest atop of the surface of the saltwater environment in which it is floating, or be slightly submerged beneath the surface of the saltwater environment in which it is floating (e.g., no more than about 12 inches). In various aspects, the bottom portion of the porous floating bioreactor is of the same transparent material or a different transparent material. Alternatively, the bottom portion, such as the bottom half which faces downward toward the flow of the saltwater environment, of the porous floating bioreactor is a non-transparent material, such as a translucent material or an opaque material. Accordingly, in one or more aspects of the present disclosure, the porous floating bioreactor may be composed of a single material in its entirety or at least two different materials (e.g., one material for the top portion and another material for the bottom portion).

In one or more aspects of the present disclosure, the top portion of the porous floating bioreactor, as described above, is transparent but may or may not be porous, whereas the bottom portion of the bioreactor is porous. Alternatively, both the top and bottom portions (the entirety) of the porous floating bioreactors described herein are porous. Accordingly, the nutrient, gaseous, and water transfer into and out of the bioreactor may be selectively controlled based on the particular selected area(s) or porosity. For example, the porous portion of the porous floating bioreactors of the present disclosure are designed to contain algae cells while allowing the transfer of water, dissolved salts, dissolved gasses, dissolved nutrients, and the like.

The volume of the porous floating bioreactors of the present disclosure is not considered to be particularly limited, but is preferably selected to contain a desired amount of cultivating algae without compromising their biological growth. In one or more aspects of the present disclosure, the volume of the porous floating bioreactors described herein may be in the range of about 1,000 liters to about 100,000 liters, encompassing any value and subset therebetween, such as about 1,000 liters to about 10,000 liters.

The shape of the porous floating bioreactors of the present disclosure is not considered to be particularly limited, but is preferably selected to allow maximum exposure to sunlight to facilitate growth and lipid production of the cultivated algae therewithin. In one or more aspects of the present disclosure, the shape of the porous floating bioreactors described herein may be a cylinder shape, a cone shape, a sphere shape, a torus shape, a cube shape, a cuboid shape, a pillow-like (e.g., a raft-like) shape, a square shape, an octahedron shape, a pyramid shape, a tetrahedron shape, a hexagonal shape, a triangular shape, a pentagonal shape, a pentagram shape, a dodecahedron shape, an icosahedron shape, a curvature shape, a serpentine shape, and the like. In one or more aspects, the porous floating bioreactor may be cylindrical, serpentine, or pillow-like in shape and have a diameter of about 4 inches (about 13 centimeters) to about 20 inches (about 51 centimeters), such as about 6 inches, or about 6 to 10 inches, or about 6 to 8 inches, encompassing any values and subset therebetween. The diameter of the porous floating bioreactor may be consistent or vary along one or more dimensions of the bioreactor, without departing from the scope of the present disclosure. One or more of such shaped and sized porous floating bioreactors may additionally be utilized to achieve the desired volumetric space for algae cultivation to meet specific facility or growth needs.

The particular pore size of the porous floating bioreactors described herein may depend on a number of factors, including the algae species being cultivated within the bioreactor; the environment in which the bioreactor is deployed; the size necessary to promote bulk transfer of water, nutrients, and carbon sources; and the like. In one or more aspects, the pore size of the porous floating bioreactors of the present disclosure may be in the range of about 0.1 micrometer ($\mu m$) to about 400 $\mu m$, encompassing any value and subset therebetween, such as in the range of about 0.1 $\mu m$ to about 300 $\mu m$, or about 0.1 $\mu m$ to about 200 $\mu m$, or about 0.1 $\mu m$ to about 100 $\mu m$, or about 0.1 $\mu m$ to about 50 $\mu m$, or about 0.1 $\mu m$ to about 25 $\mu m$, or about 0.1 $\mu m$ to about 10 $\mu m$, or about 0.5 $\mu m$ to about 10 $\mu m$, or about 0.5 to about 1 $\mu m$, encompassing any value and subset therebetween. The aforementioned pore size range(s) equally apply to the bottom portion and the top portion (if porous), without limitation.

The pore size of the porous floating bioreactors may be homogeneous or heterogeneous, provided that they are collectively able to retain the cultivating algae therein. For example, if the selected algae has a median average diameter of 20 $\mu m$, the pore sizes of the porous floating bioreactors described herein may be homogeneous or heterogeneous at any pore size in the range of about 1 $\mu m$ to less than 20 $\mu m$, encompassing any value and subset therebetween. That is, if the pores are homogeneous, they may have a median average pore size or mode average pore size of any of about 1 $\mu m$, about 2 $\mu m$, about 3 $\mu m$, about 4 $\mu m$, about 5 $\mu m$, about 6 $\mu m$, about 7 $\mu m$, about 8 $\mu m$, about 9 $\mu m$, about 10 $\mu m$, about 11 $\mu m$, about 12 $\mu m$, about 13 $\mu m$, about 14 $\mu m$, about 15 $\mu m$, about 16 $\mu m$, about 17 $\mu m$, about 18 $\mu m$, about 19 $\mu m$, or about 20 $\mu m$, encompassing any value and subset therebetween.

The shape of the pores is not considered to be particularly limited, provided that the pore sizes meet the desired average diameter. The shape of the pores may be any of those mentioned above with reference to the shape of the porous floating bioreactors described herein, such as a cylinder shape, a cone shape, a sphere shape, a torus shape, a cube shape, a cuboid shape, a pillow-like (e.g., a raft-like shape) shape, a square shape, an octahedron shape, a pyramid shape, a tetrahedron shape, a hexagonal shape, a triangular shape, a pentagonal shape, a pentagram shape, a dodecahedron shape, an icosahedron shape, a curvature shape, a serpentine shape, and the like, and any combination thereof.

Figure 2:
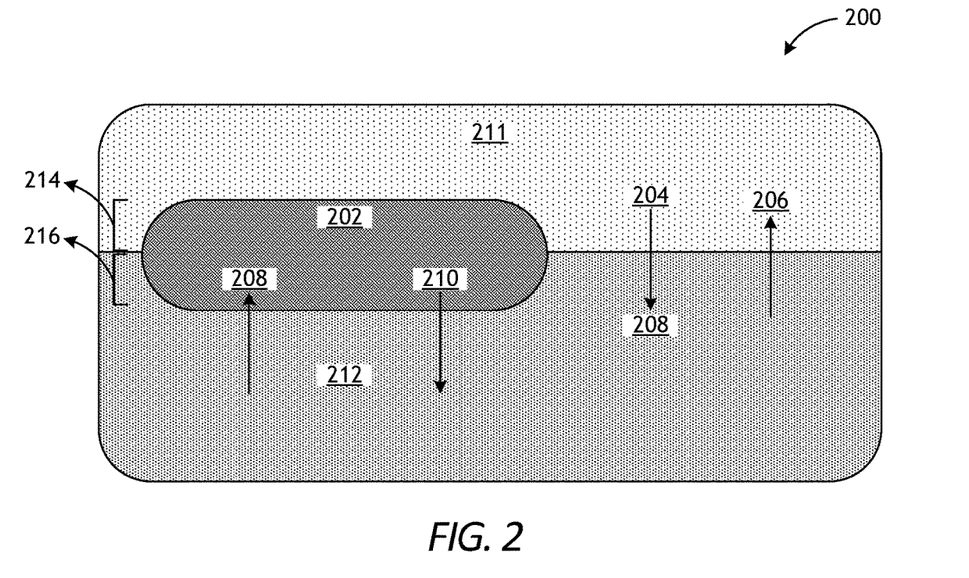
FIG. 2 is a diagram of an illustrative system in which a porous floating bioreactor exchanges nutrients within an offshore saltwater environment according to one or more aspects of the present disclosure.

Referring now to FIG. 2, illustrated is system 200 in which a porous floating bioreactor 202 is depicted floating in saltwater 212. As shown, a top portion 214 of the porous floating bioreactor 202 is exposed to atmosphere 211 (e.g., air) above the surface of the saltwater 212, whereas a bottom portion 216 of the porous floating bioreactor 202 is submerged within the saltwater 212. Carbon dioxide ($CO_2$) 204 is received into the saltwater 212 from atmosphere 211 and oxygen gas ($O_2$) 206 is expelled from the saltwater 212 into the atmosphere 211. Carbon dioxide 204 is converted into bicarbonate within the saltwater 212, and continuously replenished from the atmosphere 211. That is, the saltwater 212 and the atmosphere 211 maintain equilibrium carbon dioxide levels. Accordingly, as described hereinabove, bicarbonate 208 may be readily available within saltwater 212, such as a result of the carbon dioxide 204 therein ($CO_2 \leftrightarrow$ Bicarbonate), and may be transferred therefrom into the porous floating bioreactor 202. Dissolved carbon dioxide may also transfer from the saltwater 212 into the porous floating bioreactor alone or in addition to bicarbonate 208. In exchange, dissolved oxygen ($dO_2$) 210 may be transferred from within the porous floating bioreactor 202 and into the saltwater 212. Moreover, each of bicarbonate 208 and dissolved oxygen 210 are readily exchangeable between the interior of the porous floating bioreactor 202 and the saltwater 212, and such exchange may depend on the consumption of the algae cultivating within the porous floating bioreactor 202. As provided above, dissolved carbon dioxide is additionally readily exchangeable between the interior of the porous floating bioreactor 202 and the saltwater 212. Bulk or diffusion fluid transfer may be facilitated by naturally occurring waves from the saltwater 212 causing fluid flow across the surface of the porous floating bioreactor 202. Accordingly, the saltwater 212 is able to effectively perform direct air capture of carbon from the atmosphere 211, thereby reducing costs associated with cultivating algae and providing necessary carbon nutrient sources for use in producing biofuels and other sustainable products.

With continued reference to FIG. 2, algae cells contained within the porous floating bioreactor 202 consume the available bicarbonate 208 and dissolved carbon dioxide 204 from saltwater 212. In so doing, the pH in the porous floating bioreactor 202 increases and the bicarbonate 208 concentration in the porous floating bioreactor 202 decreases, thereby resulting in a difference in chemical potential across the porous floating bioreactor 202 and serving as an additional driving for bicarbonate 208 transfer.

The rate of carbon transfer (e.g., as bicarbonate 208) into the porous floating bioreactor 202 can further be used to calculate a target algae growth rate. For example, at a seawater 212 pH of about 8.2 and a target productivity of 10 $g/m^2/day$ of lipid production may be achieved with only 2-3 refreshes of the carbon in the bioreactor 202 per day, which may depend on one or more factors such as the saltwater 212 environment, the selected material for the porous floating bioreactor 202, the selected shape of the porous floating bioreactor, and the like, and any combination thereof.

The porous floating bioreactors of the present disclosure may be further utilized in a process (method) that separates initial biomass growth (e.g., requiring nitrogen and other supplied nutrients to increase total algae biomass) from subsequent lipid induction (e.g., utilizing nitrogen starvation to promote lipid formation). As such, the porous floating bioreactors described herein may be used for algae growth cultivation, but may also be used for lipid induction where the algae growth is performed onshore and the lipid induction is performed in an offshore saltwater environment, as described above, within the porous floating bioreactors. That is, while the present disclosure discusses separation of algae growth (onshore) and lipid induction (offshore), it is to be appreciated that both processes may be performed in the porous floating bioreactors described herein, without departing from the present disclosure.

Nitrogen depletion is thus a driver that operates to transition from an algae growth phase to an algae induction phase. The lack of nitrogen within an algae slurry may prevent cultivated algae from producing nitrogen-containing compounds and, instead, focusing on carbon addition to produce desirable lipids which do not contain nitrogen. As such, the growth phase may be performed in a traditional onshore (e.g., open or closed cultivation system) facility, controlling for growth conditions such as pH, salinity, nutrients, water turbidity, and the like. The lipid induction phase, differently, may be performed using the porous floating bioreactors of the present disclosure in an offshore saltwater environment, allowing for constant exchange of nutrients, including bicarbonate, for algae consumption, as described hereinabove.

Offshore saltwater environments include low nitrogen concentrations (and ample bicarbonate concentrations) lending these environments to prime locations for one or both of algae growth or algae lipid production. Moreover, these offshore saltwater environments provide abundant space for commercially scaled operations (i.e., less required infrastructure), while allowing reduced operational costs as described herein. For example, in a standard algae biofuels flowsheet, saltwater is supplied to an onshore cultivation system, such as an open or closed cultivation system, requiring substantial energy input for operations including mixing, gas addition, pumping, and the like, as well as substantial land, water, and carbon source requirements.

Accordingly, if algae cultivation is performed in an onshore environment, the algae may be thereafter diluted into one or more porous floating bioreactors of the present disclosure, thereby reducing nitrogen exposure and facilitating lipid production utilizing the readily available exchange of a bicarbonate carbon source. That is, during lipid induction in the offshore saltwater environment, no additional nutrients or carbon sources are required. Moreover, the total volume of the offshore saltwater environment may be substantially larger than the total volume of the onshore cultivation environment.

Figure 3:
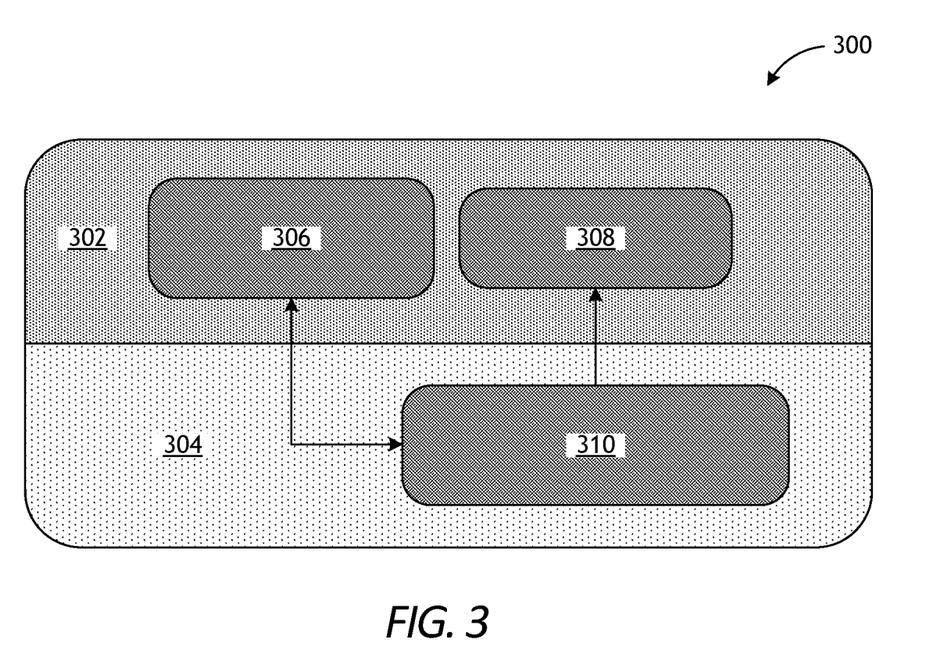
FIG. 3 is a diagram of an illustrative dual system including an onshore algae growth facility and an offshore porous floating bioreactor lipid induction area according to one or more aspects of the present disclosure.

Referring now to FIG. 3, a diagram illustrating a dual system including an onshore algae growth facility and an offshore porous floating bioreactor lipid induction area. As shown, algae growth 306 occurs onshore (i.e., land) 302. Once the algae have reached a desired confluency (i.e., concentration), the algae is transferred into one or more porous floating bioreactors 310 floating upon a surface of an offshore saltwater environment 304 (e.g., seawater; see FIG. 2) to facilitate lipid induction. Upon reaching the desired lipid concentration, the algae cells, and lipids contained therein, may be harvested to the same or different onshore 302 facility 308 for further processing, such as lipid extraction and/or other upgrading activities. As stated above, while FIG. 3 illustrates separation of algae growth (onshore) and lipid induction (offshore), it is to be appreciated that both processes may be performed in the porous floating bioreactors described herein, without departing from the present disclosure, such that the onshore algae growth 306 portion would be eliminated.

To effectively deploy the porous floating bioreactors of the present disclosure, as well as any associated piping and/or other required connections, a system of offshore saltwaterworks (e.g., marineworks) may be implemented according to one or more aspects of the present disclosure. In doing so, the porous floating bioreactors may be adequately protected from wave action, tidal action, biological threats (e.g., marine life), environmental damage or destruction, co-entanglement between bioreactors, and the like, and any combination thereof. Such deployment systems may include one or more buoys, turbidity (silt) curtains, nets, containment booms, baffle curtains, containment berms, other anchor systems, and the like, and any combination thereof.

Figure 4A:
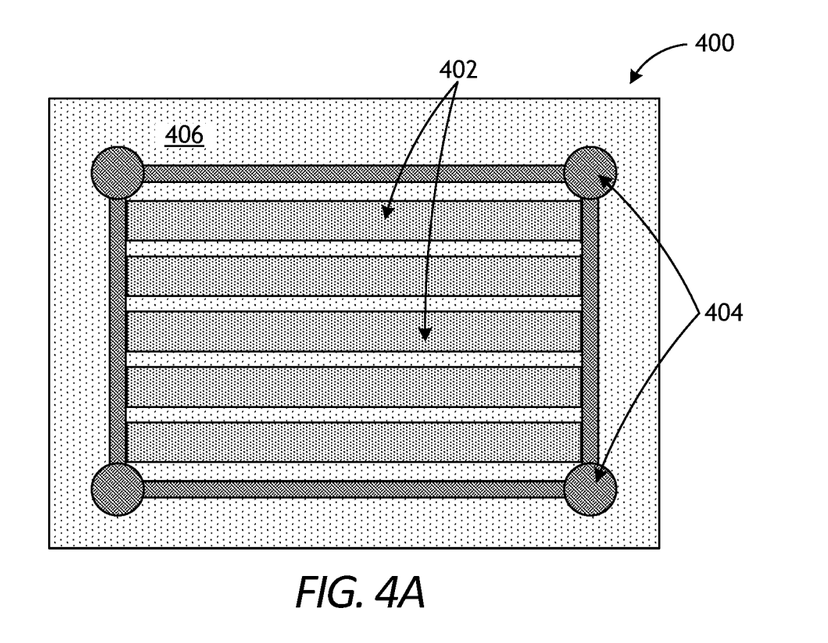
FIGS. 4A and 4B are diagrams of a top-view and a side-view, respectively, of a representative buoy system for deploying one or more of the porous floating bioreactors according to one or more aspects of the present disclosure.
Figure 4B:
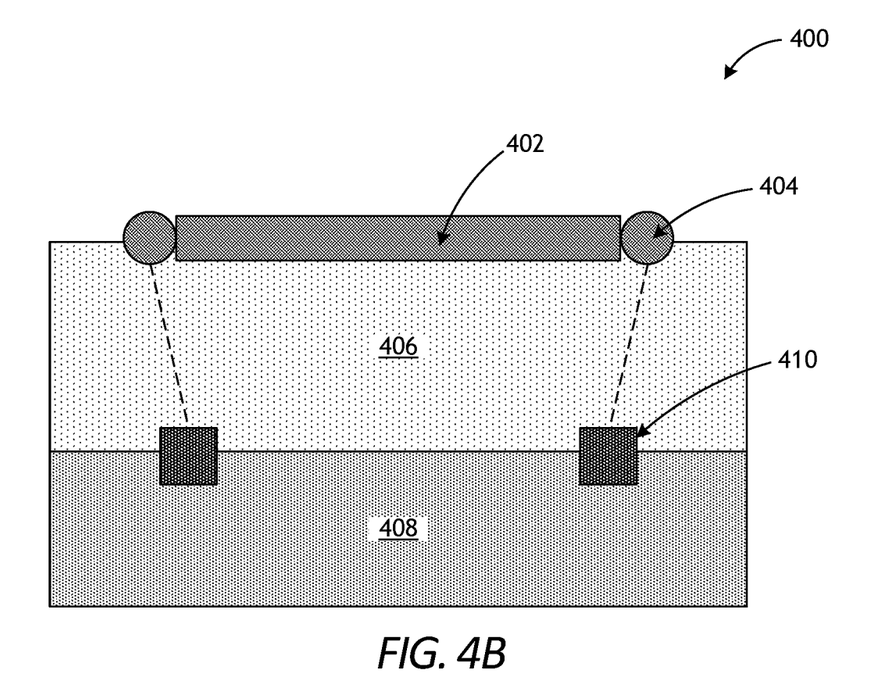

Referring now to FIGS. 4A and 4B, illustrated are diagrams of a top-view and a side-view, respectively, of a representative containment boom system 400 for deploying one or more of the porous floating bioreactors of the present disclosure. The system(s) illustrated in FIGS. 4A and 4B may be utilized to anchor one or more porous floating bioreactors 402 within an offshore saltwater environment 406 using containment booms 404, whilst controlling the amount of energy that each bioreactor 402 experiences, thereby controlling the mixing action received. As shown in FIG. 4B, the surface containment booms 404 are connected to the porous floating bioreactors 402 and are anchored via anchors 410 to the surface 408 of the offshore saltwater environment 406. The surface containment booms 404 may be anchored to the anchors 410 via nets, lines, chains, and the like. Connections between the various porous floating bioreactors 402 (see FIG. 4A) may be made using any number of connection means, such as plastic fittings, wires, lines, chains, and the like, without limitation. That is, the porous floating bioreactors 402 may be secured only to each other (or one or more of each other) or alternatively/additionally secured to the booms 404, without departing from the scope of the present disclosure and/or alternatively/additionally secured to a surface 408 of a saltwater environment 406. Additionally, various inlets and outlets (e.g., piping headers) may be utilized to allow algae cell input into the porous floating bioreactors 402 and harvesting of the cultivated algae cells out of the porous floating bioreactors 402 for downstream processing. That is, the porous floating bioreactors 402 may be in fluid communication with onshore growth facilities and/or onshore harvesting facilities (see FIG. 3) of an onshore algae processing facility.

Figure 5A:
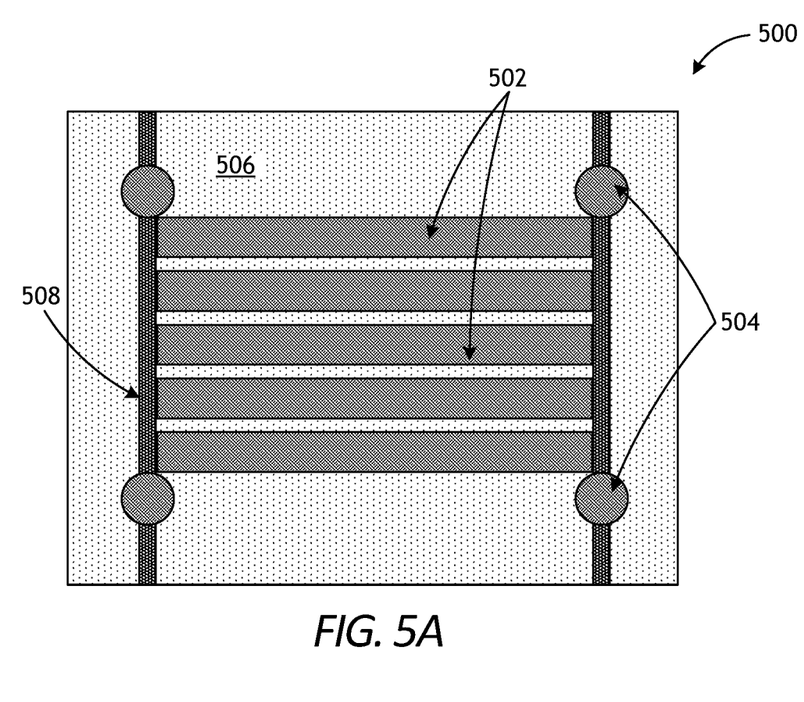
FIGS. 5A and 5B are diagrams of a top-view and a side-view, respectively, of a representative silt curtain system for deploying one or more of the porous floating bioreactors of the present disclosure.
Figure 5B:
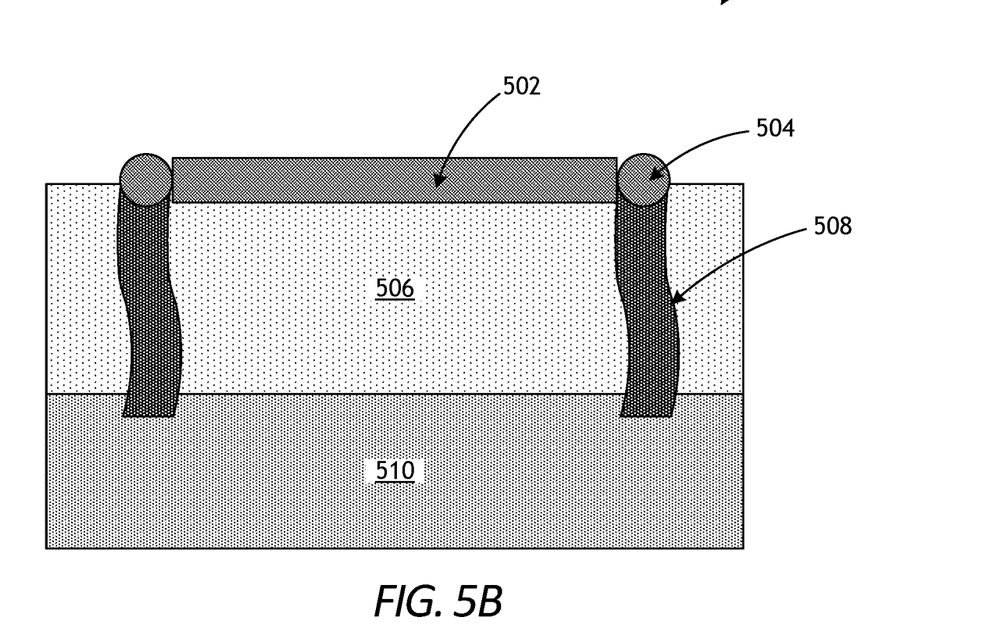

Referring now to FIGS. 5A and 5B, illustrated are diagrams of a top-view and a side-view, respectively, of a representative silt curtain system 500 for deploying one or more of the porous floating bioreactors of the present disclosure. The silt curtains 508 may be used to protect the cultivating algae from marine life, and the like, for example, whilst enabling bulk movement of water and nutrients into and out of the porous floating bioreactor 502. The system(s) illustrated in FIGS. 5A and 5B may be utilized to anchor one or more porous floating bioreactors 502 within an offshore saltwater environment 506 using buoys 504 equipped with silt curtains 508, whilst controlling the amount of energy that each bioreactor 502 experiences, thereby controlling the mixing action received, and limiting marine life, sediment, and other potential interferents from interfering with the algae within the porous floating bioreactors 502. As described above, the buoys 504 may be anchored to the surface of the offshore floor, as shown in FIG. 4B, or alternatively the buoys 504 and the silt curtains 508 may be free floating an not anchored to the surface 510 of the offshore floor, as shown in FIG. 5B, without departing from the scope of the present disclosure.

Figure 6A:
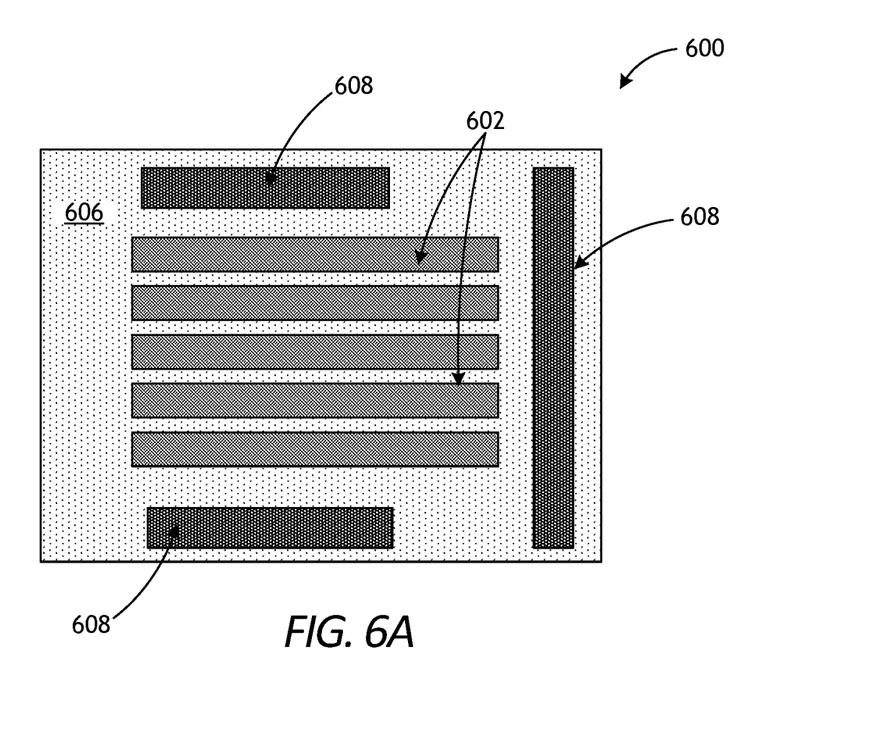
FIGS. 6A and 6B are diagrams of a top-view and a side-view, respectively, of a representative marineworks system for deploying one or more of the porous floating bioreactors of the present disclosure.
Figure 6B:
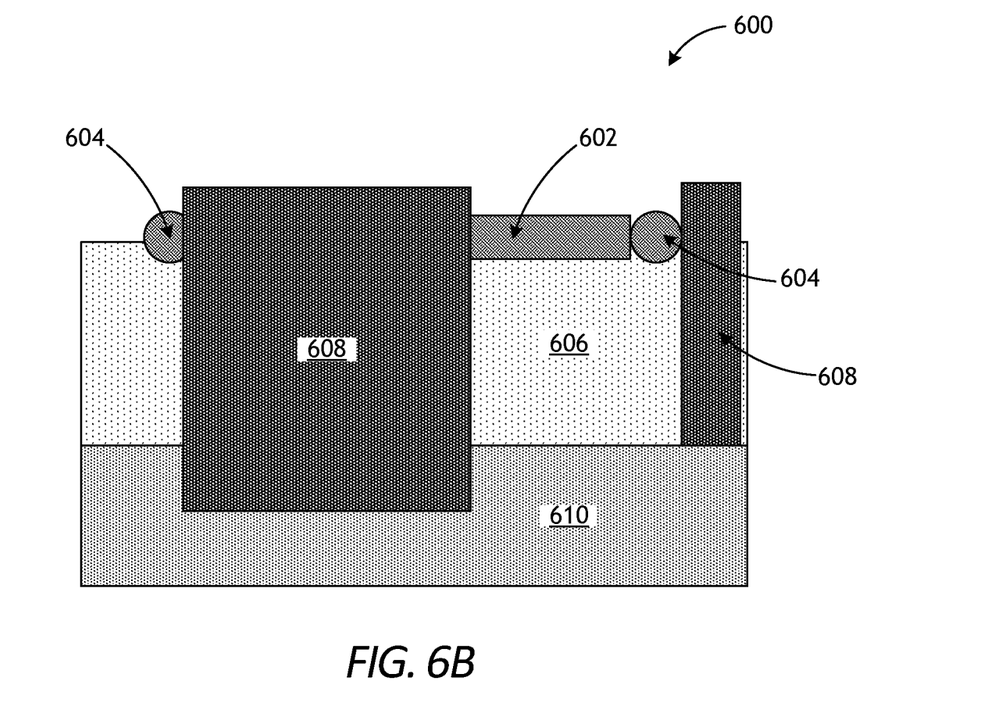

Referring now to FIGS. 6A and 6B, illustrated are diagrams of a top-view and a side-view, respectively, of a representative marineworks system 600 for deploying one or more of the porous floating bioreactors of the present disclosure. The marineworks 608 may be used to protect the cultivating algae from marine life, and the like, for example, whilst enabling bulk movement of water and nutrients into and out of the porous floating bioreactors 602 by allowing at least a portion of the bioreactor 602 to be exposed to a surrounding saltwater environment 606. That is, the marineworks 608 do not entirely surround the porous floating bioreactors 602. The marineworks 608 may be any suitable solid structure that is capable of sustained functionality (sturdiness) within the saltwater environment 606, such as rock, tire pilings, non-flexible or semi-flexible plastics, concrete (e.g., a concrete tetrapod), brick, ceramic, a non-rustable metal, and the like, and any combination thereof. The marineworks 608 may act as wave barriers to at least partially enclose the porous floating bioreactors 602, and also protect them from marine life, sediment, or other potential interferents. Further, the marineworks 608 may be movable or permanently installed into a surface 610 bearing in mind their configuration to direct wave action to maximize growth of cultivating algae (e.g., increase or reduce wave action to facilitate mixing depending on the particular saltwater environment 606), without departing from the scope of the present disclosure. Accordingly, the marineworks 608 may increase costs and complexity compared to various other configurations, such as the configurations shown in FIGS. 4A, 4B, 5A, and 5B, particularly in deeper saltwater environments 606, but may in turn provide increased wave protection and infrastructure support. As shown in FIG. 6B, the porous floating bioreactors 602 may be secured to or within a marineworks 608 structure by buoys 604 or other means, including each of which is described hereinabove.

Accordingly, the selected barrier or containment selected may be based on one or more factors, such as wave patterns; wave depths; prevailing currents and tides; the selected material, structure, and shape of the porous floating bioreactors, and the like, and any combination thereof. For example, saltwater environments with calmer, shallower waters may preferably utilize simpler options; saltwater environments with rougher, deeper waters may require more substantial protection options for the porous floating bioreactors.

As described, algae may be cultivated or induced in an algae water slurry within the porous floating bioreactors of the present disclosure. As used herein, the term "algae slurry" or "algae water slurry," and grammatical variants thereof, refers to a flowable liquid comprising at least water, algae cells, and optionally algae nutrient media (e.g., carbon, phosphorous, nitrogen, and optionally additional elemental nutrients). The water and carbon nutrients are supplied by a saltwater environment, but the remaining aspects of the slurry are provided to the interior of the porous floating bioreactors for deployment within the saltwater environment.

Algae sources for preparing the algae slurry and use within the porous floating bioreactors of the present disclosure include, but are not limited to, unicellular and multicellular algae. Examples of such algae can include, but are not limited to, a rhodophyte, chlorophyte, heterokontophyte, tribophyte, glaucophyte, chlorarachniophyte, euglenoid, haptophyte, cryptomonad, dinoflagellum, phytoplankton, and the like, and combinations thereof. In some examples, algae can be of the classes Chlorophyceae and/or Haptophyta. Examples, as well as additional or alternative algae sources may include one or more (including all) of *Achnanthes, Agmenellum, Amphiprora, Amphora, Anabaena, Anabaenopsis, Anacystis, Ankistrodesmus, Aphanizomenon, Arthrospira, Asterocapsa, Asteromonas, Auxenochlorella, Boekelovia, Borodinella, Borzia, Botryococcus, Bracteococcus, Calothrix, Carteria, Chaetoceros, Chamaesiphon, Chlamydomonas, Chlorella, Chlorococcum, Chlorogloeopsis, Chlorogonium, Chroococcidiopsis, Chroococcus, Chroomonas, Chrysosphaera, Compactochlorella, Cricosphaera, Crinalium, Crypthecodinium, Cryptomonas, Cyanobacterium, Cyanobium, Cyanocystis, Cyanospira, Cyanothece, Cyclotella, Cylindrospermopsis, Cylindrospermum, Dactylococcopsis, Dermocarpella, Dunaliella, Ellipsoidon, Emiliania, Eremosphaera, Ernodesmius, Euglena,*

*Fischerella, Fragilaria, Franceia, Fremyella, Geitleria, Geitlerinema, Gloeobacter, Gloeocapsa, Gloeothamnion, Gloeothece, Haematococcus, Halocafeteria, Halospirulina, Hymenomonas, Isochrysis, Iyengariella, Lepocinclis, Leptochlorella, Leptolyngbya, Limnothrix, Lyngbya, Marinichlorella, Micractinium, Microcoleus, Microcystis, Monoraphidium, Myxosarcina, Nannochloris, Nannochloropsis, Nanochlorum, Navicula, Neochloris, Nephrochloris, Nephroselmis, Nitzschia, Nodularia, Nostoc, Nostochopsis, Ochromonas, Oedogonium, Oocystis, Oscillatoria, Ostreococcus, Parachlorella, Pascheria, Pavlova, Phaeodactylum, Phagus, Phormidium, Picochlorum, Planktochlorella, Planktothrix, Platymonas, Pleurocapsa, Pleurochrysis, Pleurococcus, Prochlorococcus, Prochloron, Prochlorothrix, Prototheca, Pseudanabaena, Pseudochlorella, Pseudoneochloris, Pseudostaurastrum, Psuedochlorococcum, Pyramimonas, Pyrobotrys, Rivularia, Scenedesmus, Schizochlamydella, Schizothrix, Scytonema, Skeletonema, Spirulina, Spyrogyra, Stanieria, Starria, Stichococcus, Stigonema, Symploca, Synechococcus, Synechocystis, Tetrachlorella, Tetraselmis, Thalassiosira, Tolypothrix, Tribonema, Trichodesmium, Tychonema, Vaucheria, Viridiella, Volvox, Xenococcus*, and *Zoochlorella* algae species. Any combination of the aforementioned algae sources may additionally be used to prepare an algae slurry.

The optional algae nutrient media, excepting the carbon source, for use in forming an algae slurry may comprise at least nitrogen (e.g., in the form of ammonium nitrate or ammonium urea) and phosphorous. Other elemental micronutrients may also be included, such as potassium, iron, manganese, copper, zinc, molybdenum, vanadium, boron, chloride, cobalt, silicon, and the like, and any combination thereof. That is, in the saltwater environment described herein, such nutrient media may not be required for algae growth and/or lipid formation.

Accordingly, the present disclosure provides devices, methods, and systems for utilizing one or more porous floating bioreactors that can be deployed in an offshore saltwater environment that avoids land costs and land competition associated with traditional outdoor, land-based algae cultivation systems by utilizing naturally existing carbon from the saltwater environment to facilitate algae cultivation and/or induction.

The present disclosure provides, among others, the following aspects, each of which may be considered as optionally including any alternate thereof:

Clause 1: An apparatus comprising: an offshore porous floating bioreactor for containing an algae water slurry in a saltwater environment and having a top portion and a bottom portion, wherein at least a portion of the top portion is composed of a first transparent material and at least a portion of the bottom portion is porous, comprising a plurality of pores.

Clause 2: The apparatus of Clause 1, wherein at least a portion of the bottom portion is composed of a second transparent material.

Clause 3: The apparatus of Clause 2, wherein the first transparent material and the second transparent material are the same or different.

Clause 4: The apparatus of any of Clause 2 to Clause 3, wherein the first transparent material and the second transparent material are selected from the group consisting of polyethylene, cellulose acetate, polypropylene, ethylene vinyl acetate, polyurethane, nylon, polyvinyl acetate, polytetrafluoroethylene, and any combination thereof.

Clause 5: The apparatus of Clause 1, wherein at least a portion of the bottom portion is composed of a translucent or opaque material.

Clause 6: The apparatus of Clause 5, wherein the translucent or opaque material is selected from the group consisting of polyethylene, cellulose acetate, polypropylene, polyvinyl acetate, ethylene vinyl acetate, polyurethane, nylon, polyvinyl acetate, polytetrafluoroethylene, and any combination thereof.

Clause 7: The apparatus of any of the preceding Clauses, wherein the plurality of pores of the bottom portion have a pore size in the range of about 0.1 micrometer to about 400 micrometers.

Clause 8: The apparatus of Clause 7, wherein the pore size is homogeneous or heterogeneous.

Clause 9: The apparatus of any of the preceding Clauses, wherein the plurality of pores of the bottom portion have a pore shape consisting of a cylinder shape, a cone shape, a sphere shape, a torus shape, a cube shape, a cuboid shape, a pillow-like shape, a square shape, an octahedron shape, a pyramid shape, a tetrahedron shape, a hexagonal shape, a triangular shape, a pentagonal shape, a pentagram shape, a dodecahedron shape, an icosahedron shape, a curvature shape, a serpentine shape, and any combination thereof.

Clause 10: The apparatus of any of the preceding Clauses, wherein at least a portion of the top portion is porous, comprising a plurality of pores.

Clause 11: The apparatus of Clause 10, wherein the plurality of pores of the top portion have a pore size in the range of about 0.1 micrometer to about 400 micrometers.

Clause 12: The apparatus of any of Clause 11, wherein the pore size is homogeneous or heterogeneous.

Clause 13: The apparatus of any of Clause 10 to Clause 12, wherein the plurality of pores of the top portion have a pore shape consisting of a cylinder shape, a cone shape, a sphere shape, a torus shape, a cube shape, a cuboid shape, a pillow-like shape, a square shape, an octahedron shape, a pyramid shape, a tetrahedron shape, a hexagonal shape, a triangular shape, a pentagonal shape, a pentagram shape, a dodecahedron shape, an icosahedron shape, a curvature shape, a serpentine shape, and any combination thereof.

Clause 14: The apparatus of any of the preceding Clauses, wherein the offshore porous floating bioreactor has a volume in the range of about 1,000 liters gallon to about 100,000 liters.

Clause 15: The apparatus of any of the preceding Clauses, wherein the offshore porous floating bioreactor has a cylinder shape, a cone shape, a sphere shape, a torus shape, a cube shape, a cuboid shape, a pillow-like shape, a square shape, an octahedron shape, a pyramid shape, a tetrahedron shape, a hexagonal shape, a triangular shape, a pentagonal shape, a pentagram shape, a dodecahedron shape, an icosahedron shape, a curvature shape, or a serpentine shape.

Clause 16: The apparatus of any of Clause 1 to Clause 14, wherein the offshore porous floating bioreactor has a cylindrical shape, a serpentine shape, or a pillow-like shape, and further has a diameter in the range of about 4 inches to about 50 inches.

Clause 17: A method comprising: deploying at least one offshore porous floating bioreactor in a saltwater environment, wherein the at least one offshore porous floating bioreactor comprises a top portion and a bottom portion, and at least a portion of the top portion is composed of a transparent material and at least a portion of the bottom portion is porous, comprising a plurality of pores; performing at least one of cultivation or lipid induction of an algae water slurry contained in the at least one offshore porous floating bioreactor.

Clause 18: The method of Clause 17, wherein at least a portion of the bottom portion is composed of a second transparent material.

Clause 19: The method of Clause 17, wherein the first transparent material and the second transparent material are the same or different.

Clause 20: The method of any of Clause 18 to Clause 19, wherein the first transparent material and the second transparent material are selected from the group consisting of polyethylene, cellulose acetate, polypropylene, ethylene vinyl acetate, polyurethane, nylon, polyvinyl acetate, polytetrafluoroethylene, and any combination thereof.

Clause 21: The method of Clause 17, wherein at least a portion of the bottom portion is composed of a translucent or opaque material.

Clause 22: The method of Clause 21, wherein the translucent or opaque material is selected from the group consisting of polyethylene, cellulose acetate, polypropylene, polyvinyl acetate, ethylene vinyl acetate, polyurethane, nylon, polyvinyl acetate, polytetrafluoroethylene, and any combination thereof.

Clause 23: The method of any of Clause 17 to Clause 22, wherein the plurality of pores of the bottom portion have a pore size in the range of about 0.1 micrometer to about 400 micrometers.

Clause 24: The method of Clause 23, wherein the pore size is homogeneous or heterogeneous.

Clause 25: The method of any of Clause 17 to Clause 24, wherein the plurality of pores of the bottom portion have a pore shape consisting of a cylinder shape, a cone shape, a sphere shape, a torus shape, a cube shape, a cuboid shape, a pillow-like shape, a square shape, an octahedron shape, a pyramid shape, a tetrahedron shape, a hexagonal shape, a triangular shape, a pentagonal shape, a pentagram shape, a dodecahedron shape, an icosahedron shape, a curvature shape, a serpentine shape, and any combination thereof.

Clause 26: The method of any of Clause 17 to Clause 25, wherein at least a portion of the top portion is porous, comprising a plurality of pores.

Clause 27: The method of Clause 26, wherein the plurality of pores of the top portion have a pore size in the range of about 0.1 micrometer to about 400 micrometers.

Clause 28: The method of any of Clause 26 to Clause 27, wherein the pore size is homogeneous or heterogeneous.

Clause 29: The method of any of Clause 26 to Clause 28, wherein the plurality of pores of the top portion have a pore shape consisting of a cylinder shape, a cone shape, a sphere shape, a torus shape, a cube shape, a cuboid shape, a pillow-like shape, a square shape, an octahedron shape, a pyramid shape, a tetrahedron shape, a hexagonal shape, a triangular shape, a pentagonal shape, a pentagram shape, a dodecahedron shape, an icosahedron shape, a curvature shape, a serpentine shape, and any combination thereof.

Clause 30: The method of any of Clause 17 to Clause 29, wherein the offshore porous floating bioreactor has a volume in the range of about 1,000 liters gallon to about 100,000 liters.

Clause 31: The method of any of Clause 17 to Clause 30, wherein the offshore porous floating bioreactor has a cylinder shape, a cone shape, a sphere shape, a torus shape, a cube shape, a cuboid shape, a pillow-like shape, a square shape, an octahedron shape, a pyramid shape, a tetrahedron shape, a hexagonal shape, a triangular shape, a pentagonal shape, a pentagram shape, a dodecahedron shape, an icosahedron shape, a curvature shape, or a serpentine shape.

Clause 32: The method of any of Clause 17 to Clause 30, wherein the offshore porous floating bioreactor has a cylindrical shape, a serpentine shape, or a pillow-like shape, and further has a diameter in the range of about 4 inches to about 50 inches.

Clause 33: The method of any of Clause 17 to Clause 32, further comprising exchanging at least one of bicarbonate and dissolved carbon dioxide from the saltwater environment into the at least one offshore porous floating bioreactor through the plurality of pores.

Clause 34: The method of Clause 33, wherein the algae water slurry comprises algae cells that consume at least one of the bicarbonate and the dissolved carbon dioxide during cultivation or lipid induction of an algae water slurry contained in the at least one offshore porous floating bioreactor.

Clause 35: The method of any of Clause 17 to Clause 34, wherein at least a portion of the top portion of the at least one offshore porous floating bioreactor is above a surface of the saltwater environment or floating no more than about 12 inches below the surface of the saltwater environment, thereby exposing the algae water slurry contained in the at least one offshore porous floating bioreactor to sunlight through first transparent material.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the incarnations of the present disclosure. At the very least, and not as an attempt to limit the application of the doctrine of equivalents to the scope of the claim, each numerical parameter should at least be construed in light of the number of reported significant digits and by applying ordinary rounding techniques.

One or more illustrative incarnations incorporating one or more elements are presented herein. Not all features of a physical implementation are described or shown in this application for the sake of clarity. It is understood that in the development of a physical aspect incorporating one or more elements of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

While compositions and methods are described herein in terms of "comprising" various components or steps, the compositions and methods can also "consist essentially of" or "consist of" the various components and steps.

Therefore, the present disclosure is well adapted to attain the ends and advantages mentioned as well as those that are inherent therein. The particular examples and configurations disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative examples disclosed above may be altered, combined, or modified and all such variations are considered within the scope and spirit of the present disclosure. The aspects illustratively disclosed herein suitably may be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

What is claimed is:

1. An apparatus comprising:
an offshore porous floating bioreactor for containing an algae water slurry in a saltwater environment comprising a top portion and a bottom portion, the top portion and the bottom portion comprising an entirety of the bioreactor, the top portion comprising less than half of the bioreactor, wherein the top portion is composed of a first transparent material, and wherein the bottom portion is porous, comprising a plurality of pores, the plurality of pores of the bottom portion having a pore size of about 0.1 micrometer to about 400 micrometers.

2. The apparatus of claim 1, wherein at least a portion of the bottom portion is composed of a second transparent material.

3. The apparatus of claim 2, wherein the first transparent material and the second transparent material are the same or different.

4. The apparatus of claim 3, wherein the first transparent material and the second transparent material are selected from the group consisting of polyethylene, cellulose acetate, polypropylene, ethylene vinyl acetate, polyurethane, nylon, polyvinyl acetate, polytetrafluoroethylene, and any combination thereof.

5. The apparatus of claim 1, wherein the bottom portion is composed of a translucent or opaque material.

6. The apparatus of claim 5, wherein the translucent or opaque material is selected from the group consisting of polyethylene, cellulose acetate, polypropylene, polyvinyl acetate, ethylene vinyl acetate, polyurethane, nylon, polyvinyl acetate, polytetrafluoroethylene, and any combination thereof.

7. The apparatus of claim 1, wherein the pore size is homogeneous or heterogeneous.

8. The apparatus of claim 1, wherein the plurality of pores of the bottom portion have a pore shape consisting of a cylinder shape, a cone shape, a sphere shape, a torus shape, a cube shape, a cuboid shape, a pillow-like shape, a square shape, an octahedron shape, a pyramid shape, a tetrahedron shape, a hexagonal shape, a triangular shape, a pentagonal shape, a pentagram shape, a dodecahedron shape, an icosahedron shape, a curvature shape, a serpentine shape, and any combination thereof.

9. The apparatus of claim 1, wherein the top portion is porous, comprising a plurality of pores.

10. The apparatus of claim 9, wherein the plurality of pores of the top portion have a pore size of about 0.1 micrometer to about 400 micrometers.

11. The apparatus of claim 10, wherein the pore size is homogeneous or heterogeneous.

12. The apparatus of claim 9, wherein the plurality of pores of the top portion have a pore shape consisting of a cylinder shape, a cone shape, a sphere shape, a torus shape, a cube shape, a cuboid shape, a pillow-like shape, a square shape, an octahedron shape, a pyramid shape, a tetrahedron shape, a hexagonal shape, a triangular shape, a pentagonal shape, a pentagram shape, a dodecahedron shape, an icosahedron shape, a curvature shape, a serpentine shape, and any combination thereof.

13. The apparatus of claim 1, wherein the offshore porous floating bioreactor has a volume in the range of about 1,000 liters gallon to about 100,000 liters.

14. The apparatus of claim 1, wherein the offshore porous floating bioreactor has a cylinder shape, a cone shape, a sphere shape, a torus shape, a cube shape, a cuboid shape, a pillow-like shape, a square shape, an octahedron shape, a pyramid shape, a tetrahedron shape, a hexagonal shape, a triangular shape, a pentagonal shape, a pentagram shape, a dodecahedron shape, an icosahedron shape, a curvature shape, or a serpentine shape.

15. The apparatus of claim 1, wherein the offshore porous floating bioreactor has a cylindrical shape, a serpentine shape, or a pillow-like shape, and further has a diameter in the range of about 4 inches to about 50 inches.

16. A method comprising:
deploying at least one offshore porous floating bioreactor in a saltwater environment, wherein the at least one offshore porous floating bioreactor comprises a top portion and a bottom portion, the top portion and the bottom portion comprising an entirety of the bioreactor, the top portion comprising less than half of the bioreactor, wherein the top portion is composed of a transparent material, and wherein the bottom portion is porous, comprising a plurality of pores, the plurality of pores of the bottom portion having a pore size of about 0.1 micrometer to about 400 micrometers; and
performing at least one of cultivation or lipid induction of an algae water slurry contained in the at least one offshore porous floating bioreactor.

17. The method of claim 16, further comprising exchanging at least one of bicarbonate and dissolved carbon dioxide from the saltwater environment into the at least one offshore porous floating bioreactor through the plurality of pores.

18. The method of claim 17, wherein the algae water slurry comprises algae cells that consume at least one of the bicarbonate and the dissolved carbon dioxide during cultivation or lipid induction of an algae water slurry contained in the at least one offshore porous floating bioreactor.

19. The method of claim 16, wherein at least a portion of the top portion of the at least one offshore porous floating bioreactor is above a surface of the saltwater environment or floating no more than about 12 inches below the surface of the saltwater environment, thereby exposing the algae water slurry contained in the at least one offshore porous floating bioreactor to sunlight through first transparent material.

20. An apparatus comprising:
an offshore porous floating bioreactor for containing an algae water slurry in a saltwater environment comprising a vessel having a top portion and a bottom portion, the top portion and the bottom portion comprising an entirety of the vessel, wherein the top portion and the bottom portion are composed of a transparent, porous material comprising a plurality of pores, the plurality of pores having a pore size of about 0.1 micrometer to about 400 micrometers.

* * * * *